Figure 2:
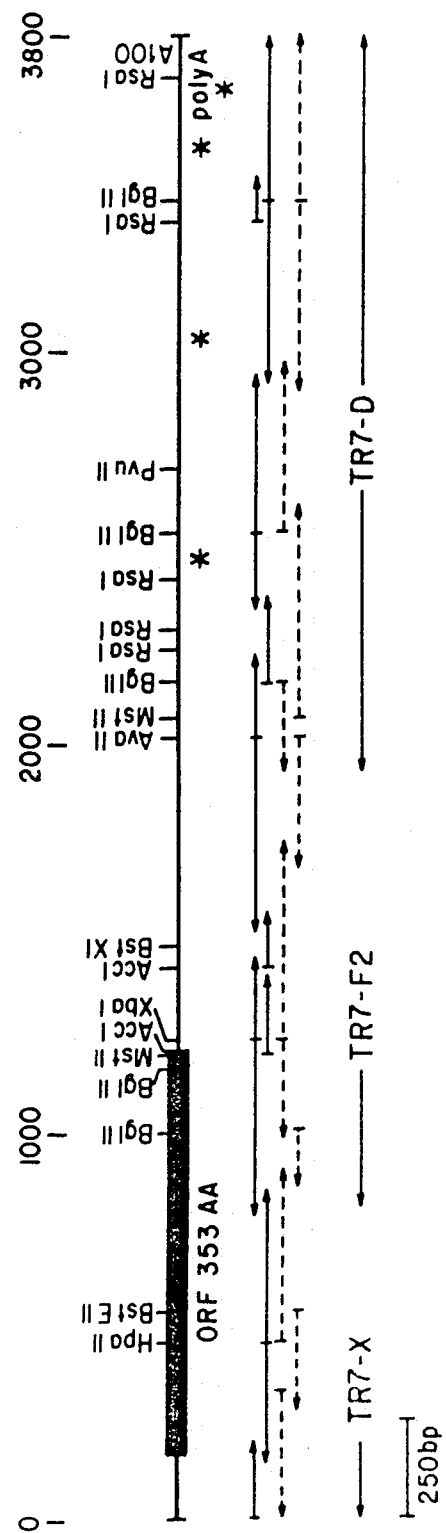

United States Patent [19]

Cantor et al.

[11] Patent Number: 4,952,499
[45] Date of Patent: Aug. 28, 1990

[54] GENES AND THEIR ENCODED PROTEINS WHICH REGULATE GENE EXPRESSION OF THE INTERLEUKIN-2 RECEPTOR AND OF HUMAN LYMPHOTROPIC RETROVIRUSES

[75] Inventors: Harvey I. Cantor, Wellesley; Roberto Patarca, Brookline, both of Mass.

[73] Assignee: Dana-Farber Cancer Institute, Boston, Mass.

[21] Appl. No.: 154,758

[22] Filed: Feb. 11, 1988

[51] Int. Cl.$^5$ .................. C12P 21/00; C12P 21/02; C12P 19/34; C12N 15/00
[52] U.S. Cl. .................. 435/172.3; 435/91; 435/172.1; 435/320; 435/252.33; 435/240.2; 435/69.1; 435/320; 435/252.33; 435/240.2; 435/69.1
[58] Field of Search .................. 435/60, 70, 91, 172.1, 435/172.3, 320; 530/350; 536/27; 935/18, 32, 36, 58, 60, 70, 71

[56] References Cited

U.S. PATENT DOCUMENTS 4,738,922 4/1988 Hazeltine et al. .

OTHER PUBLICATIONS

Patarca et al., 1988, Proc. Natl. Acad. Sci. U.S.A., 85:2733-2737.
Ruben et al., 1988, Science, 241:89-92.
Hidaka et al., 1988, EMBO J., 7:519-523.
Varmus, 1988, Chem. Abstracts, (abstract No. 109:206821w), 109:265.
Inoue et al., 1987, Chem. Abstracts, (abstract No. 108:55577b), 107:422.
Siekevitz et al., 1987, Science, 238:1575-1578.
Tong-Starksen et al., 1987, Proc. Natl. Acad. Sci. U.S.A., 84:6845-6849.
Nabel and Baltimore, 1987, Nature, 326:711-713.
Jones et al., 1986, Science, 232:755-759.
Zagury et al., 1986, Science, 231:850-853.
Folks et al., 1986, Science, 231:600-602.
Leonard et al., 1985, Science, 230:633-639.
Nikaido et al., 1984, Nature, 311:631-635.

Primary Examiner—Thomas G. Wiseman
Assistant Examiner—Joan Ellis
Attorney, Agent, or Firm—Pennie & Edmonds

[57] ABSTRACT

The present invention is directed to genes, termed Rpt-1 (regulatory protein T lymphocyte-1), which are expressed at higher levels by resting CD4+ helper/inducer T cells relative to activated CD4+ cells. The invention also relates to the proteins encoded by such genes, termed rpt-1 proteins, which regulate gene expression directed by the promoter region of the interleukin-2 receptor (IL-2r) alpha chain gene or by the promoter region of the long terminal repeat of human lymphotropic retroviruses such as the human immunodeficiency virus type 1 (HIV-1) human T cell leukemia virus (HTLV)-I, and HTLV-II. In particular, rpt-1 proteins down-regulate gene expression controlled by the promoter of the IL-2r alpha chain gene or by the promoter of the long terminal repeat of HIV-1. The proteins and nucleic acids of the invention have value in diagnosis and therapy of immune disorders such as AIDS.

In a specific example of the present invention, an Rpt-1 gene and its encoded intracellular protein of approximately 41,000 daltons molecular weight are described. The rpt-1 protein is shown to be selectively expressed by activated CD4+ T cells, and to down-regulate gene expression of the IL-2r and the HIV-1.

23 Claims, 6 Drawing Sheets

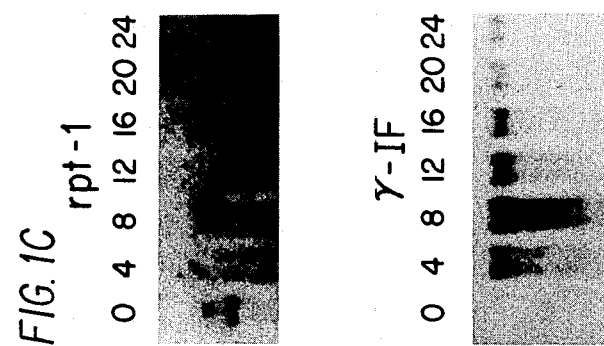
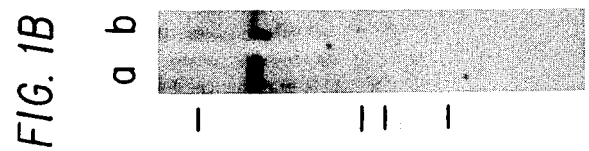
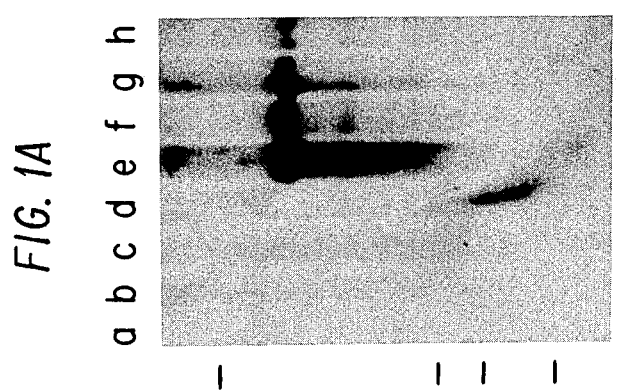

FIG. 2 CONT.

FIG. 4B
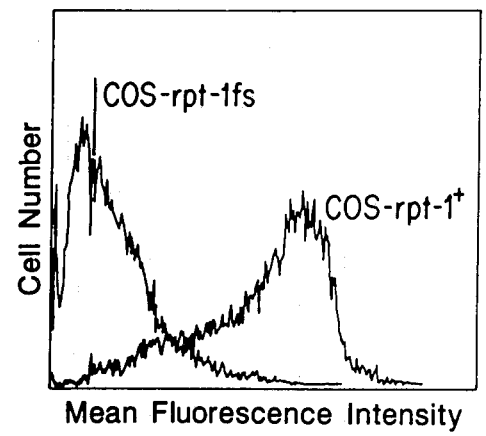
FIG. 4A
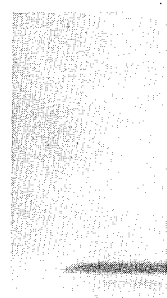
—58,000
—48,500
—36,500
FIG. 4C

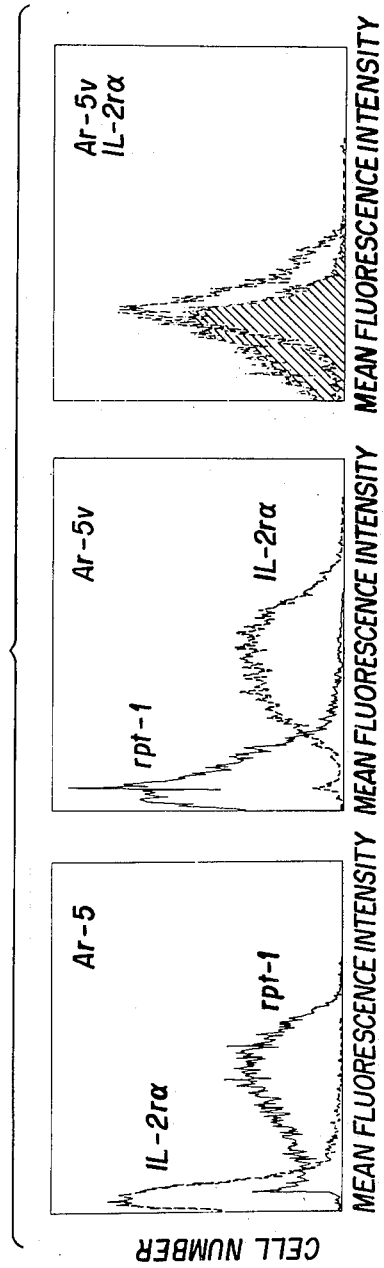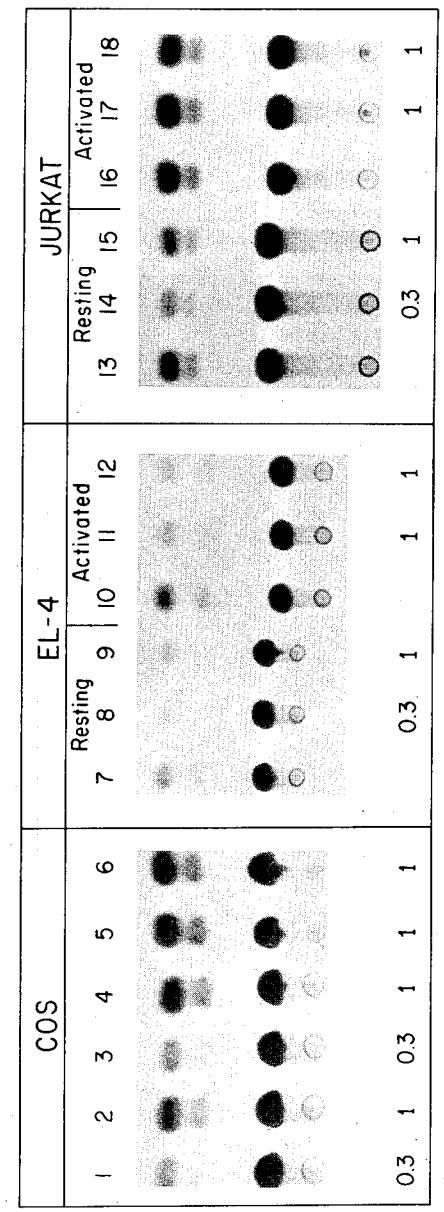
FIG. 6A
FIG. 6B

GENES AND THEIR ENCODED PROTEINS WHICH REGULATE GENE EXPRESSION OF THE INTERLEUKIN-2 RECEPTOR AND OF HUMAN LYMPHOTROPIC RETROVIRUSES

Pursuant to the provisions of 35 U.S.C. §202(c), it is hereby acknowledged that the Government has certain rights in this invention, which was made in part with funds from the National Institutes of Health.

TABLE OF CONTENTS

1. Introduction
2. Background of the Invention
   2.1. T Cell Gene Expression
   2.2. The Interleukin-2 Receptor
   2.3. Human Immunodeficiency Virus Type I and Other Human Retroviruses
3. Summary of the Invention
   3.1. Definitions
4. Description of the Figures
5. Detailed Description of the Invention
   5.1. Isolation of the Rpt-1 Gene
   5.2. Expression of the Rpt-1 Gene
   5.3. Identification and Purification of the Expressed Gene Product
   5.4. Structure of the Rpt-1 Gene and Protein
      5.4.1. Genetic Analysis
      5.4.2. Protein Analysis
   5.5 Regulation of Gene Expression of the Interleukin-2 Receptor and of Human Lymphotropic Retroviruses
   5.6. Anti-Rpt-1 Antibody Production
   5.7. Rpt-1 Related Derivatives, Analogues, and Peptides
   5.8. Uses of Rpt-1
      5.8.1. Diagnosis
      5.8.2. Therapy
6. Cloning and Characterization of the Rpt-1 Gene and its Encoded Protein
   6.1 Materials and Methods
      6.1.1. Cells
      6.1.2. Activation of T Cells
      6.1.3. Production of a T Cell Probe
      6.1.4. Construction of a T Cell cDNA Library
      6.1.5. Nucleic Acid Blotting and Hybridization
      6.1.6. Western Blot Analysis
      6.1.7. Plasmids
      6.1.8. Transfection of Cell Lines and Chloramphenicol Acetyl Transferase Assays
      6.1.9. Immunofluorescence
   6.2. Results
   6.3. Discussion
7. Deposit of Microorganisms

1. INTRODUCTION

The present invention is directed to genes, termed Rpt-1 (regulatory protein T lymphocyte-1), which are expressed at higher levels by resting CD4+ inducer T cells relative to activated CD4+ cells. The invention also relates to proteins encoded by such genes, termed rpt-1 proteins, which regulate gene expression directed by the promoter region of the interleukin-2 receptor alpha chain gene or by the promoter region of the long terminal repeat of human lymphotropic retroviruses. The proteins and nucleic acids of the invention have value in diagnosis and therapy of immune disorders such as AIDS.

2. BACKGROUND OF THE INVENTION

2.1. T Cell Gene Expression

Analysis of cellular and viral proteins produced by clones of inducer, cytotoxic, and suppressor T cells, has shown that each T cell subset is genetically programmed to specify particular patterns of protein synthesis before and after activation by antigen (Nabel, G., et al., 1981, Cell 23:19–28; Fresno, M., et al., 1982, Cell 30:707–713; Zagury, D., et al., 1986, Science 231:860–863). For instance, the levels of expression of the retrovirus associated with the acquired immunodeficiency syndrome (AIDS), HIV-1, are markedly increased upon activation of infected inducer T cells (Zagury, D., et al., 1986, Science 231:860–863; Klatzmann, D. and Gluckman, J.C., 1986, Immunol. Today 7:291–296; Nabel, G. and Baltimore, D., 1987, Nature 326:711–713; Tong-Starksen, S. E., et al., 1987, Proc. Natl. Acad. Sci. U.S.A. 84:6845). An intracellular protein that regulates genes expressed in resting and activated T cells has been described (e.g., Nabel, G. and Baltimore, D., 1987, Nature 326:711–713; Tong-Starksen, S. E., et al., 1987, Proc. Natl. Acad. Sci. U.S.A. 84:6845).

2.2. The Interleukin-2 Receptor

T cells secrete a variety of polypeptides affecting immunoregulation of hematopoietic cells and are themselves subject to regulation by hormone peptides interacting with specific receptors on their cell surface. Interleukin-2, originally termed T cell growth factor, is synthesized and secreted by antigen- or lectin-activated T lymphocytes in the presence of macrophage-derived interleukin-1, and interacts with specific high-affinity membrane receptors to exert its biological effects (Smith, K. A., 1980, Immunol. Rev. 51:337–357; Leonard, W. J., et al., 1983, Proc. Natl. Acad. Sci. U.S.A. 80:6957–6961). The interleukin-2 receptor (IL-2r, Tac antigen) is not present on the surface of resting T or B lymphocytes. Upon activation by specific antigens or mitogens, T cell proliferation is mediated by an autocrine mechanism whereby activated cells secrete interleukin-2 (IL-2) and also express cell surface receptors for IL-2 (IL-2r) (Mier, J. W. and Gallo, R. C., 1980, Proc. Natl. Acad. Sci. U.S.A. 77:6134; Robb, R. J., et al., 1981, J. Exp. Med. 154:1455; Leonard, W. J., et al., 1982, Nature 300:267; Meuer, S. C., et al., 1984, Proc. Natl. Acad. Sci. U.S.A. 81:1509; Tsudo, M., et al., 1984, J. Exp. Med. 160:612–617; Waldmann, T. A., et al., 1984, J. Exp. Med. 160:1450–1466).

Interaction of IL-2 with its cell surface receptor results in a continuous T cell proliferation (Greene, W. C. and Leonard, W. J., 1986, Ann. Rev. Immunol. 4:69–95; Smith, K. A., 1984, Ann. Rev. Immunol. 2:319–333). Measurement of IL-2r provides information on the state of immune activation of the lymphoid population. This has been accomplished by measuring IL-2r on cell surfaces using flow cytometry or fluorescence microscopy. Using monoclonal antibodies which define the IL-2 receptor, altered IL-2r expression has been reported in a number of immune abnormalities (Greene and Leonard, supra; Depper, J. M., et al., 1984, J. Immunol. 133:1691–1695) such as certain B- or T-cell malignancies, including Burkitt's lymphoma (Waldmann, T. A., et al., 1984, J. Exp. Med. 160:1450–1466), hairy cell leukemia (Waldmann et al., supra; Korsmeyer, S. J., et al., 1983, Proc. Natl. Acad. Sci. U.S.A. 80:4522–4526, and human T cell leukemia virus (HTLV)-I-associated adult T cell leukemia (Depper, J. M., et al., 1984, J. Immunol. 133:169114 1695). In several cases of common, pre-B or T cell acute lymphoblastic leukemia (ALL), malignant cells have been induced to express IL-2r after in vitro activation (Touw, I., et al., 1985, Blood 66:556–561; Touw, I., et al., 1986, Blood 68:1088–1094; Matsuoka, M., et al., 1986, Leuk. Res. 10:597–603) and, in some cases, interleukin-2 stimulated subsequent colony formation of neoplastic progenitor cells in vitro (Touw, 1985, supra; Touw, 1986, supra).

Leukemic cells from some patients with T cell chronic lymphocytic leukemia were shown to have the receptors and a good proliferative response to exogenous interleukin-2 (Uchiyama, T., et al., 1985, J. Clin. Invest. 76:446–453; Tsudo, M., 1986, Blood 67:316–321). However, HTLV-1 associated adult T cell leukemic cells constitutively expressed high levels of cell surface IL-2r but had no or very poor proliferative responses to interleukin-2 (Uchiyama, 1985, supra; Arya, S. K., et al., 1984, Science 223:1086–1087). Ebert et al. (1985, Clin. Immunol. Immunopathol. 37:283–297) have reported that T cells from patients with AIDS virus lack the ability to express IL-2r on their surface even when the cell is activated.

Secondary signals in T cell activation such as interleukin-1 are provided by monocytes or other accessory cells, and are required for IL-2 secretion (Schmidtke, J. R. and Hatfield, S., 1976, J. Immunol. 116:357; Maizel, A. L., et al., 1981, J. Exp. Med. 153:470; Williams, J. M., et al., 1985, J. Immunol. 135:2249).

2.3. Human Immunodeficiency Virus Type I And Other Human Retroviruses

Retroviruses are enveloped RNA tumor viruses (for a review, see Hayward, W. S. and Neel, B. G., 1981, Curr. Top. Microbiol. Immunol. 91:217–276). The virus particle consists of a ribonucleoprotein core enclosed by an outer membrane envelope derived from the host cell plasma membrane. Viral envelope glycoproteins protrude from the outer envelope. The viral genome consists of a single-stranded RNA molecule.

The long terminal repeat (LTR) region of retroviruses is found at the ends of the proviral DNA, and consists of three defined segments: U3 (derived from the 3' end of genomic RNA, R (a short terminal repeat of genomic RNA), and U5 (derived from the 5' end of genomic RNA). The promoter for retroviral RNA synthesis appears to be located within the LTR, in the U3 region (id.). The LTR regions of several HTLV isolates have been analyzed (Sodroski, J., et al., 1984, in Human T-Cell Leukemia/Lymphoma Virus, Gallo, R. C., et al., eds., Cold Spring Harbor Laboratory, Cold Spring Harbor, N.Y., pp. 149–155).

HTLV-I and HTLV-II are related but distinct human retroviruses associated with certain leukemias and lymphomas. HTLV-I is causatively linked to adult T cell leukemia (Gallo, R. C. and Wong-Staal, F., 1982, Blood 60:545; Gallo, R. C., 1984, in Cancer Surveys, Vol. 3, Franks, L. M., et al., eds., Oxford Univ. Press, Oxford, pp. 113–159). HTLV-II was first identified in a patient with a T cell variant of hairy cell leukemia (Kalyanaraman, V. S., et al., 1982, Science 218:571). Both viruses show a tropism for human T cells, and have the capacity to transform infected T cells in vitro, in addition to causing other cellular changes (see Arya, S. K., et al., 1984, Science 225:927–930, and references cited therein).

The causative agent of AIDS is a retrovirus, now termed human immunodeficiency virus type 1 (HIV-1), and formerly termed HTLV III (Gallo, R. C., et al., 1984, Science 224:500, Popovic, M., et al., 1984, Science 224:497), LAV (Barre-Sinoussi, F., et al., 1983, Science 220:868; Feorino, P. M., et al., 1984, Science 225:69), and ARV (Levy, J. A., et al., 1984, Science 225:840) by the three groups which independently isolated viruses which are probably of the same retrovirus subgroup (Levy, J. A., et al., 1984, Science 225:840). HIV-1 appears to infect T4+ helper T lymphocytes, and evidence suggests that the T4 antigen is the receptor or a component of the receptor for the virus (Dagleish, A. G., et al., 1984, Nature 312:763; Klatzmann, D., et al., 1984, Nature 312:767).

The structure of the RNA genome of HIV-1 has been described (Ratner, L., et al., 1985, Nature 313:277–284) and includes the gag (group-specific antigens; encoding internal structural proteins), pol (encoding the reverse transcriptase), env (encoding the envelope glycoproteins), sor (short open reading frame), 3'-orf (Guy, B., et al., 1987, Nature 330:266–269), art/trs, and tat (Kao, S.-Y., et al., 1987, Nature 330:489–493) genes.

AIDS is a disease which is characterized by a severe immune deficiency primarily caused by a decreased cell-mediated immune response (Gottlieb, M., et al., 1981, N. Engl. J. Med. 305:1425; Masur, J., et al., 1981, N. Engl. J Med. 305:1431). The immunodeficient state is characterized by a decrease in $T_H$ (T helper) lymphocytes, a reversal of the normal T4+:T8+ cell ratio, lymphopenia, and opportunistic infections often caused by *Pneumocystis carinii*. Some patients also develop lymphoma or Kaposi's sarcoma at increased incidence. The disease is usually fatal.

3. SUMMARY OF THE INVENTION

The present invention is directed to genes, termed Rpt-1 (regulatory protein T lymphocyte-1), which are expressed at higher levels by resting CD4+ helper/inducer T cells relative to activated CD4+ cells. The invention also relates to the proteins encoded by such genes, termed rpt-1 proteins, which regulate gene expression directed by the promoter region of the interleukin-2 receptor (IL-2r) alpha chain gene or by the promoter region of the long terminal repeat of human lymphotropic retroviruses such as human immunodeficiency virus type-1 (HIV-1), human T cell leukemia virus (HTLV)-I, and HTLV-II. In particular, rpt-1 proteins down-regulate gene expression controlled by the promoter of the IL-2r alpha chain gene or by the promoter of the long terminal repeat of HIV-1 The proteins and nucleic acids of the invention have value in diagnosis and therapy of immune disorders such as AIDS.

In a specific example of the present invention detailed infra, an Rpt-1 gene and its encoded intracellular protein of approximately 41,000 daltons molecular weight are described. The rpt-1 protein is shown to be selectively expressed by activated CD4+ T cells, and to down-regulate gene expression of the IL-2r and the HIV-1.

| 3.1. DEFINITIONS | |
|---|---|
| bp | = base pair |
| CAT | = chloramphenicol acetyl transferase |
| ConA | = concanavalin A |
| FACS | = fluorescence activated cell sorter |
| FITC | = fluorescein isothiocyanate |
| HBB | = hemoglobin b chain |

3.1. DEFINITIONS -continued

| | | |
|---|---|---|
| HIV | = | human immunodeficiency virus |
| HTLV | = | human T cell leukemia virus |
| IL | = | interleukin |
| IL-2r | = | interleukin-2 receptor |
| kb | = | kilobase pair |
| KLH | = | keyhole limpet hemocyanin |
| LTR | = | long terminal repeat |
| PBS | = | phosphate-buffered saline |
| PHA | = | phytohemagglutinin |
| RFLP | = | restriction fragment length polymorphism |
| Rpt-1 | = | regulatory protein T-lymphocyte-1 |
| TPA | = | 12-0-tetradecanoylphorbol 13-acetate |
| TSA | = | Tris saline azide |

4. DESCRIPTION OF THE FIGURES

FIG. 1A. Expression of Rpt-1 in lymphocyte clones. 5 ug of poly(A)+ RNA from each cell type were analyzed by electrophoresis on a 1.5% agarose gel, transferred to nitrocellulose, and hybridized with a $^{32}P$-labeled probe prepared by nick translation of the 3.7 kb cDNA insert of pcD-rpt1. Cell types: MOPC 315, a murine myeloma (lane a); Cl.NK1.1, a Thy 1+ natural killer cell clone (lane b); Cl.Ly23.4, a suppressor T cell clone with (lane c) or without (lane d) ConA; Cl.Ly1-T1, a T-helper clone without (lane e) and with (lane f) ConA; and Cl.Ly1-N5, a T-helper clone without (lane g) and with (lane h) ConA. RNA was obtained 15 hours after activation. As determined by densitometric scanning, the intensity of the radioactive signal in lanes f and h is approximately 50% of that in lanes e and g, respectively, even when the levels of actin mRNA are used as internal controls for normalization. Molecular weight markers correspond to: 6000, 1765, 1426, and 920 bases.

FIG. 1B. Expression of Rpt-1 in heterogeneous lymphocyte populations. 5 ug of poly(A)+ RNA from splenocytes (lane a) or thymocytes (lane b) was hybridized with the Rpt-1 insert as described above.

FIG. 1C. Time course of Rpt-1 expression upon activation of the T cell clone Cl.Ly1-T1.5 ug of total RNA was obtained from Cl.Ly1-T1 at the indicated times (hours) after stimulation by antigen (TNP-BGG; trinitrophenyl-bovine gamma-globulin) and splenic adherent cells. Northern blots were hybridized with a nick-translated probe corresponding to the 5' 1.3 kb RsaI-XbaI fragment (coding region) of Rpt-1 (upper panel) and to gamma-interferon (lower panel).

FIG. 2. Restriction map of the insert of pcD-rpt1 and sequence of the coding region. The sequence was determined by the method of Maxam and Gilbert (1977, Proc. Natl. Acad. Sci. U.S.A. 74:560–564) and was confirmed in its entirety on both strands. The restriction map includes arrows to indicate the extent and direction of sequence determined, and asterisks to denote potential polyadenylation sites. TCR7-D and TCR7-F2 are partial cDNA clones and TCR7-X is a full-length cDNA clone. Cysteine and histidine residues in the predicted amino acid sequence that may be involved in metal finger formation are circled. The first methionine, the predicted most hydrophilic region (amino acid residue numbers 205–210) and putative nuclear localization signal (amino acid numbers 268–276) are boxed.

Figure 3:
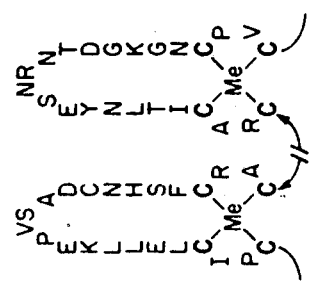

FIG. 3. Hydrophilicity plot of the predicted rpt-1 protein (Hopp, T. and Woods, K., 1981, Proc. Natl. Acad. Sci. U.S.A. 78:3824–3828). Above the horizontal line, hydrophilic; below, hydrophobic. Potential finger structures including the pairs of cysteine and histidine residues marked above the plot (circled in FIG. 2) are schematized in the lower panel (Me: metal). The location of the predicted most hydrophilic region in rpt-1 (KKEKKE) is shown (black box) as well as the subsequence similar to the nuclear localization signal of the SV40 large T antigen (NL) (Sabatini, D.D., et al., 1982, J. Cell. Biol. 92:1–19).

FIG. 4A. Western blot of mourse spleen cell extracts using anti-KKEKKE antibody. Molecular weight markers (Sigma Chemical Co.) correspond to: 58,000; 48,500; and 36,500 daltons.

FIG. 4B. COS7m6 cells were transfected with 6 ug of either pcD-rpt1 (COS-rpt1+) or pcD-rpt1fs (COS-rpt1fs). The FACS fluorescence profile of an aliquot of each cell population after incubation with the anti-KKEKKE antibody is shown. Slot blot analysis of RNA from both groups of COS7m6 cells revealed equal amounts of mRNA that hybridized to the Rpt-1 probe.

FIG. 4C. Immunofluorescence of both cell populations was also examined using a fluorescence microscope. COS-rpt-1 transfectants showed predominantly nuclear fluorescence as illustrated in the photomicrograph. Fluorescence was not detectable in the COS-rpt1fs cells.

Figure 5:
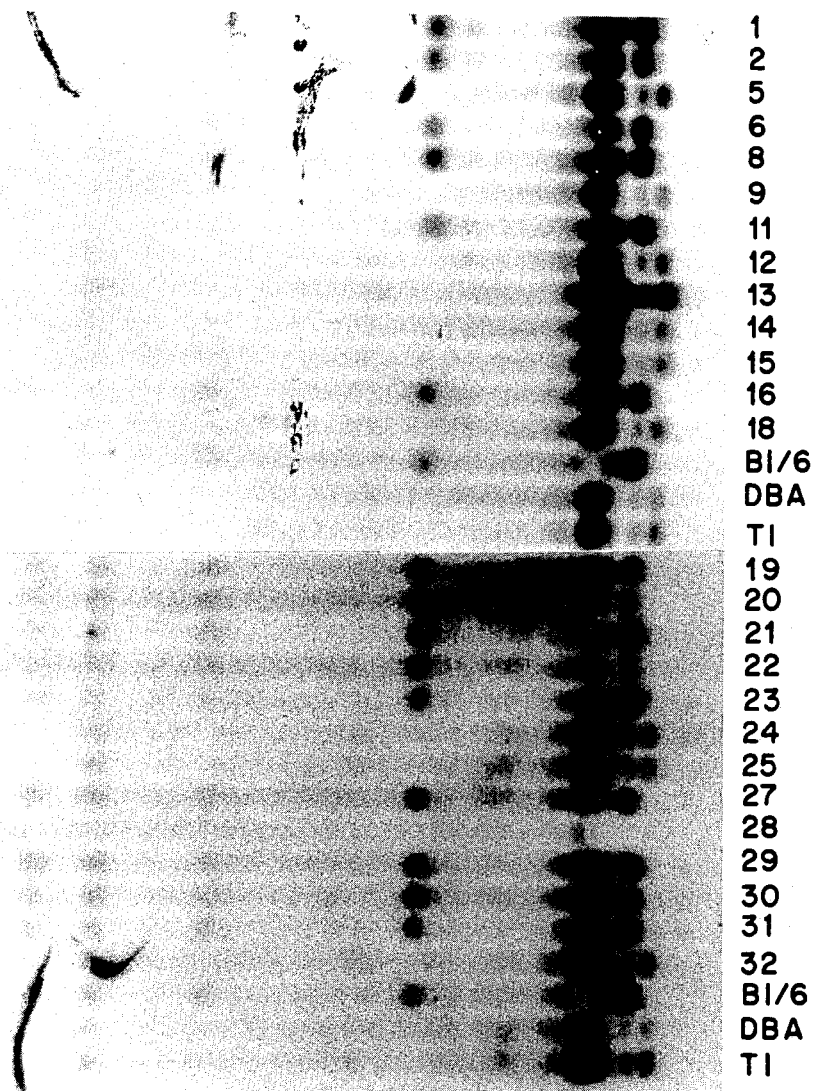

FIG. 5. Southern blot analysis of liver. Genomic DNA from C57B1/6 (B), DBA (D), Cl.Ly1-T1 (BALB/c), and the numbered recombinant inbred strains derived from B and D parental strains (BXD) (Jackson Laboratories, Bar Harbor, Me.) (Taylor, B. A., 1981, in Genetic Variants and Strains of the Laboratory Mouse, Academic Press, New York, pp. 397–407) were digested with HindIII. The genomic DNA was analyzed in a 0.7% agarose gel, and blotted onto a Zeta-probe membrane (BioRad, Richmond, Calif.). The filter was hybridized with a $^{32}P$-labelled probe prepared by nick translation of the 5' 1.3 kb RsaI-XbaI fragment (coding region) of pcD-rpt1.

FIG. 6A. Indirect immunofluorescent staining and FACS analysis of rpt-1 and IL-2rα expression by clones Ar-5 (left panel) and Ar-5v (center panel). IL-2rα fluorescence of Ar-5 was at background levels comparable to that obtained using a control antibody. Twenty-four hours after stimulation with recombinant IL-2, aliquots of Ar-5v were transfected with 6 ug of pcD, pcD-rpt1fs, or pcD-rpt1 48 hours before measurement of surface Il-2rα by FACS analysis (right panel). Approximately one-third of the cells transfected with pcD-rpt1 (hatched bars), but not cells transfected with pcD-rpt1fs, no longer expressed significant levels of IL-2rα (compare to IL-2rα FACS profile of Ar-5, left panel). The levels of IL-2rα expressed by cells transfected with pcD-rpt1fs (shown in the right panel) did not differ significantly from those of cells transfected with pcD or with pcD-beta-galactosidase. Slot blot analysis of 250 ug total RNA showed that cells transfected with pcD-rpt1 and pcD-rpt1fs, but not pcD (or pcD-beta-galactosidase), contained high levels of Rpt-1 mRNA. All of these transfectants had similar levels of IL-3 mRNA.

FIG. 6B. Chloramphenicol acetyl transferase (CAT) assays of COS7m6, and resting and activated EL-4 and Jurkat cells. T cells were activated 20 hours before the CAT assays. CAT reaction mixtures were incubated for 20 minutes. Results are shown after transfection with the following plasmids: COS7m6 cells: 4 ug of IL2r-pCAT (plasmid containing the IL-2rα promoter upstream of the bacterial chloramphenicol gene [CAT]) co-transfected with 6 ug of either pcD-rpt1 (lane 1) or pcD-rpt1fs (lane 2); 3 ug of pLTR-1CAT (plasmid containing the HIV-1 LTR upstream of CAT), co-transfected with 6 ug of either pcD-rpt1 (lane 3) or pcD-rpt1fs (lane 4); 2 ug of pSV2CAT co-transfected with 6 ug of either pcD-rpt1 (lane 5) or pcD-rpt1fs (lane 6). EL-4 cells: 5 ug of pLTR-1CAT and 4 ug of pSV7fdtat cotransfected alone (lanes 7, 10), or with 6 ug of either pcD-rpt1 (lanes 8, 11) or pcD-rpt1fs (lanes 9, 12). Jurkat cells: 5 ug of pLTR-1CAT and 2 ug of pSV7fdtat cotransfected alone (lanes 13, 16) or with 3 ug of either pcD-rpt1 (lanes 14, 17) or pcD-rpt1fs (lanes 15, 18). The inhibitory effect of rpt-1 was also seen when using half (3 ug) and twice (9 ug) the amount of pcD-rpt1, and it did not depend on the amount of indicator and poD-rpt1 plasmids used as long as the ratio of their amounts remained the same as above. Cotransfections that included the pcD vector displayed lower CAT activity levels due to competition between promoters for transcriptional factors. The chloramphenicol conversion (%) after co-transfection with pcD-rpt1 is expressed as a proportion of the chloramphenicol conversion (%) obtained after co-transfection with pcD-rpt1fs with the same CAT plasmid. Chloramphenicol conversion (%) obtained with pcD-rpt1fs cotransfections were assigned a value of 1. Lanes 7, 10, 13, and 16 are included as controls for T cell activation. Extracts from cells that had not been transfected with CAT plasmids showed no CAT activity. Each experiment was repeated three to five times. Standard errors of absolute chloramphenicol conversion percentages obtained in each experiment were less than 30% of the mean.

5. DETAILED DESCRIPTION OF THE INVENTION

The present invention is directed to genes, termed Rpt-1 (regulatory protein T lymphocyte-1), which are expressed at higher levels by resting CD4+ helper/inducer T cells relative to activated CD4+ cells. The invention also relates to the proteins encoded by such genes, termed rpt-1 proteins, which regulate gene expression directed by the promoter region of the interleukin-2 receptor (IL-2r) alpha chain gene or by the promoter region of the long terminal repeat (LTR) of human lymphotropic retroviruses such as human immunodeficiency virus type 1 (HIV-1), human T cell leukemia virus (HTLV)-I, and HTLV-II. In particular, rpt-1 proteins down-regulate gene expression controlled by the promoter of the IL-2r alpha chain gene or by the promoter of the LTR of HIV-1. The proteins and nucleic acids of the invention have value in diagnosis and therapy of immune disorders such as AIDS.

In a specific example of the present invention detailed infra, an Rpt-1 gene and its encoded intracellular protein of approximately 41,000 daltons molecular weight are described. The rpt-1 protein is shown to be selectively expressed by activated CD4+ T cells, and to down-regulate gene expression of the IL-2r and the HIV-1.

5.1 Isolation of the Rpt-1 Gene

Any mammalian cell can potentially serve as the nucleic acid source for the molecular cloning of the Rpt-1 gene. Isolation of the Rpt-1 gene involves the isolation of those DNA sequences which encode a protein displaying Rpt-1-associated structure or properties, e.g., down-regulation of gene expression of the IL-2r or the HIV-1 (see Section 5.5, infra). The DNA may be obtained by standard procedures known in the art from cloned DNA (e.g., a DNA "library"), by chemical synthesis, by cDNA cloning, or by the cloning of genomic DNA, or fragments thereof, purified from the desired mammalian cell. (See, for example, Maniatis et al., 1982, Molecular Cloning, A Laboratory Manual, Cold Spring Harbor Laboratory, Cold Spring Harbor, N.Y.; Glover, D. M. (ed.), 1985, DNA Cloning: A Practical Approach, MRL Press, Ltd., Oxford, U.K., Vol. I, II.) Clones derived from genomic DNA may contain regulatory and intron DNA regions in addition to coding regions; clones derived from cDNA will contain only exon sequences. Whatever the source, the Rpt-1 gene should be molecularly cloned into a suitable vector for propagation of the gene.

In the molecular cloning of the gene from genomic DNA, DNA fragments are generated, some of which will encode the desired Rpt-1 gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the Rpt-1 gene may be accomplished in a number of ways. For example, if an amount of an Rpt-1 gene or its specific RNA, or a fragment thereof, is available and can be purified and labeled, the generated DNA fragments may be screened by nucleic acid hybridization to the labeled probe (Benton, W. and Davis, R., 1977, Science 196:180; Grunstein, M. and Hogness, D., 1975, Proc. Natl. Acad. Sci. U.S.A. 72:3961). Those DNA fragments with substantial homology to the probe will hybridize. If a purified Rpt-1-specific probe is unavailable, nucleic acid fractions enriched in Rpt-1 may be used as a probe, as an initial selection procedure. As an example (see Section 6.1.3, infra), the probe representing T cell cDNA from which messages expressed by activated T cells have been subtracted can be used. It is also possible to identify the appropriate fragment by restriction enzyme digestion(s) and comparison of fragment sizes with those expected according to a known restriction map if such is available. Further selection on the basis of the properties of the gene, or the physical, chemical, or immunological properties of its expressed product, as described infra, can be employed after the initial selection.

The Rpt-1 gene can also be identified by mRNA selection by nucleic acid hybridization followed by in vitro translation. In this procedure, fragments are used to isolate complementary mRNAs by hybridization. Such DNA fragments may represent available, purified Rpt-1 DNA, or DNA that has been enriched for Rpt-1 sequences (e.g., cDNA enriched for messages of resting T cells). Immunoprecipitation analysis or functional assays (e.g., for IL-2r or HIV-1 promoter regulation) of the in vitro translation products of the isolated mRNAs identifies the mRNA and, therefore, the complementary DNA fragments that contain the Rpt-1 sequences. In addition, specific mRNAs may be selected by adsorption of polysomes isolated from cells to immobilized antibodies specifically directed against an rpt-1 protein. A radiolabeled Rpt-1 cDNA can be synthesized using the selected mRNA (from the adsorbed polysomes) as a template. The radiolabeled mRNA or cDNA may then be used as a probe to identify the Rpt-1 DNA fragments from among other genomic DNA fragments.

Alternatives to isolating the Rpt-1 genomic DNA include, but are not limited to, chemically synthesizing the gene sequence itself from a known sequence or making cDNA to the mRNA which encodes the Rpt-1 gene. For example, RNA for cDNA cloning of the Rpt-1 gene can be isolated from cells including but not limited to immune cells such as T cells. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid or pcD/Okayama-Berg plasmid (Okayama, H. and Berg, P., 1983, Mol. Cell. Biol. 3:280-289) derivatives. Recombinant molecules can be introduced into host cells via transformation, transfection, infection, electroporation, etc.

In a particular embodiment, the Rpt-1 gene expressed in resting T cells can be cloned by selection from a constructed sublibrary that contains cDNA inserts that are selectively expressed by CD4+ T helper/inducer cells. Such a procedure is described in Sections 6.1.1 through 6.1.4, infra.

In an alternative method, the Rpt-1 gene may be identified and isolated after insertion into a suitable cloning vector, in a "shot gun" approach Enrichment for the Rpt-1 gene, for example, by size fractionation, can be done before insertion into the cloning vector.

The Rpt-1 gene is inserted into a cloning vector which can be used to transform, transfect, or infect appropriate host cells so that many copies of the gene sequences are generated. In a specific embodiment, the cloning vector can be the pcD vector (Okayama-Berg vector; Okayama, H. and Berg, P., 1983, Mol. Cell. Biol. 3:280-289). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and Rpt-1 gene may be modified by homopolymeric tailing.

Identification of the cloned Rpt-1 gene can be accomplished in a number of ways based on the properties of the DNA itself, or alternatively, on the physical, immunological, or functional properties of its encoded protein. For example, the DNA itself may be detected by plaque or colony nucleic acid hybridization to labeled probes (Benton, W. and Davis, R., 1977, Science 196:180; Grunstein, M. and Hogness, D., 1975, Proc. Natl. Acad. Sci. U.S.A. 72:3961). Alternatively, the presence of the Rpt-1 gene may be detected by assays based on properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, down-regulation of IL-2r or HIV-1 promoter activity, or antigenic properties as known for rpt-1. If an antibody to rpt-1 is available, the rpt-1 protein may be identified by binding of labeled antibody to the putatively rpt-1-synthesizing clones, in an ELISA (enzyme-linked immunosorbent assay)-type procedure.

In specific embodiments, transformation of host cells with recombinant DNA molecules that incorporate the isolated Rpt-1 gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

In a particular embodiment, Rpt-1 cDNA clones in a pcD vector (Okayama, H. and Berg, P., 1983, Mol. Cell. Biol. 3:280-289) can be transfected into COS (monkey kidney) cells for large-scale expression (see Section 6.1.8, infra).

If the ultimate goal is to insert the gene into virus expression vectors such as vaccinia virus or adenovirus, the recombinant DNA molecule that incorporates the Rpt-1 gene can be modified so that the gene is flanked by virus sequences that allow for genetic recombination in cells infected with the virus so that the gene can be inserted into the viral genome.

After the Rpt-1 DNA-containing clone has been identified, grown, and harvested, its DNA insert may be characterized as described in Section 5.4.1, infra.

When the genetic structure of the Rpt-1 gene is known, it is possible to manipulate the structure for optimal use in the present invention. For example, promoter DNA may be ligated 5' of the rpt-1-coding sequence, in addition to or replacement of the native promoter to provide for increased expression of the protein. Many manipulations are possible, and within the scope of the present invention.

5.2. Expression of the Rpt-1 Gene

The nucleotide sequence coding for an rpt-1 protein or a portion thereof, can be inserted into an appropriate expression vector, i.e., a vector which contains the necessary elements for the transcription and translation of the inserted protein-coding sequence. The necessary transcriptional and translation signals can also be supplied by the native Rpt-1 gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. The expression elements of these vectors vary in their strength and specificities. Depending on the host-vector system utilized, any one of a number of suitable transcription and translation elements may be used. For instance, when cloning in mammalian cell systems, promoters isolated from the genome of mammalian cells or from viruses that grow in these cells may be used. Promoters produced by recombinant DNA or synthetic techniques may also be used to provide for transcription of the inserted sequences.

Specific initiation signals are also required for efficient translation of inserted protein coding sequences. These signals include the ATG initiation codon and adjacent sequences. In cases where the entire Rpt-1 gene including its own initiation codon and adjacent sequences are inserted into the appropriate expression vectors, no additional translational control signals may be needed. However, in cases where only a portion of the Rpt-1 coding sequence is inserted, exogenous translational control signals, including the ATG initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination).

Expression vectors containing Rpt-1 gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to the inserted Rpt-1 gene. In the second approach, the recombinant vector/host system can be identified and selected based upon the presence or absence of certain "marker" gene gunctions (e.g., thymidine kinase activity, resistance to antibiotics, transformation phenotype, occlusion body formation in baculovirus, etc.) caused by the insertion of foreign genes into the vector. For example, if the Rpt-1 gene is inserted within the marker gene sequence of the vector, recombinants containing the Rpt-1 insert can be identified by the absence of the marker gene function. In the third approach, recombinant expression vectors can be identified by assaying the foreign gene product expressed by the recombinant. Such assays can be based on the physical, immunological, or functional properties of the gene product.

Once a particular recombinant DNA molecule is identified and isolated, several methods known in the art may be used to propagate it. Once a suitable host system and growth conditions are established, recombinant expression vectors can be propagated and prepared in quantity.

In a particular embodiment detailed in the examples of the present invention, pcD vectors with an Rpt-1 cDNA insert can be transfected into COS cells, in which the Rpt-1 cDNA insert is expressed to produce the rpt-1 protein. However, the invention is not limited to the expression of Rpt-1 from pcD vectors in COS cells. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the chimeric gene product in the specific fashion desired. Expression from certain promoters can be elevated in the presence of certain inducers; thus, expression of the genetically engineered rpt-1 protein may be controlled. Furthermore, different host cells have characteristic and specific mechanisms for the translational and post-translational processing and modification of proteins. Appropriate cell lines or host systems can be chosen to ensure the desired modification and processing of the expressed heterologous protein. For example, in one embodiment, expression in a bacterial system can be used to produce the 41.3 kd rpt-1 protein with the deduced amino acid sequence of FIG. 2. In another embodiment, mammalian COS cells can be used to ensure "native" conformation of the heterologous rpt-1 protein. Furthermore, different vector/host expression systems may effect processing reactions such as proteolytic cleavages to different extents. Many such variously processed rpt-1 proteins can be produced and are within the scope of the present invention.

5 3. Identification and Purification of the Expressed Gene Product

Once a recombinant which expresses the Rpt-1 gene is identified, the gene product should be analyzed. This can be achieved by assays based on the physical, immunological, or functional properties of the product.

Once the rpt-1 protein is identified, it may be isolated and purified by standard methods including chromatography (e.g., ion exchange, affinity, and sizing column chromatography), centrifugation, differential solubility, or by any other standard technique for the purification of proteins.

Alternatively, once an rpt-1 protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105–111).

In particular embodiments of the present invention, such rpt-1 proteins, whether produced by recombinant DNA techniques or by chemical synthetic methods, include but are not limited to those containing, as a primary amino acid sequence, all or part of the amino acid sequence substantially as depicted in FIG. 2, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are rpt-1 proteins which are differentially modified during or after translation, e.g., by glycosylation, proteolytic cleavage, etc.

5.4. Structure of the Rpt-1 Gene and Protein

The structure of the Rpt-1 gene and protein can be analyzed by various methods known in the art.

5.4.1. Genetic Analysis

The cloned DNA or cDNA corresponding to the Rpt-1 gene can be analyzed by methods including but not limited to Southern hybridization (Southern, E. M., 1975, J. Mol. Biol. 98:503–517), Northern hybridization (see e.g., Freeman et al., 1983, Proc. Natl. Acad. Sci. U.S.A. 80:4094–4098), restriction endonuclease mapping (Maniatis, T., 1982, Molecular Cloning, A Laboratory Manual, Cold Spring Harbor Laboratory, Cold Spring Harbor, N.Y.), and DNA sequence analysis. Southern hybridization with an Rpt-1-specific probe can allow the detection of the Rpt-1 gene in various cell types. In one embodiment, Southern hybridization can be used to determine the genetic linkage of Rpt-1 (see Section 6.2). Northern hybridization analysis can be used to determine the expression of the Rpt-1 gene. Various cell types, at various states of development or activity can be tested for Rpt-1 expression. Such a technique and its results, demonstrating Rpt-1 expression by inducer T cells, but not by suppressor or cytolytic T cells, or by natural killer cells, are described in Sections 6.1.5 and 6.2, infra. The stringency of the hybridization conditions for both Southern and Northern hybridization can be manipulated to ensure detection of nucleic acids with the desired degree of relatedness to the specific Rpt-1 probe used.

Restriction endonuclease mapping can be used to roughly determine the genetic structure of the Rpt-1 gene. In a particular embodiment, cleavage with restriction enzymes can be used to derive the restriction map shown in FIG. 2, infra. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger, F., et al., 1977, Proc. Natl. Acad. Sci. U.S.A. 74:5463), or use of an automated DNA sequenator (e.g., Applied Biosystems, Foster City, Calif.). The cDNA sequence of a representative Rpt-1 gene comprises the sequence substantially as depicted in FIG. 2, and described in Section 6.2, infra.

5.4.2. Protein Analysis

The amino acid sequence of the rpt-1 protein can be derived by deduction from the DNA sequence, or alternatively, by direct sequencing of the protein, e.g., with an automated amino acid sequencer. The amino acid sequence of a representative rpt-1 protein comprises the sequence substantially as depicted in FIG. 2, and detailed in Section 6.2, infra.

The rpt-1 protein sequence can be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the rpt-1 protein and the corresponding regions of the gene sequence which encode such regions. A hydrophilicity profile of the rpt-1 protein described in the examples section infra is depicted in FIG. 3.

Secondary structural analysis (Chou, P. and Fasman, G., 1974, Biochemistry 13:222) can also be done, to identify regions of rpt-1 that assume specific secondary structures.

Other methods of structural analysis can also be employed. These include but are not limited to X-ray crystallography (Engstom, A., 1974, Biochem. Exp. Biol. 11:7–13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5. Regulation of Gene Expression of the Interleukin-2 Receptor and of Human Lymphotropic Retroviruses The rpt-1 proteins function to regulate the level of gene expression directed by the promoters of the interleukin-2 receptor or of the LTRs of human lymphotropic retroviruses such as HIV-1, HTLV-I, and HTLV-II (see Sections 6.2 and 6.3, infra). Expression of the Rpt-1 gene results in the decreased expression of genes whose transcription is under the control of the IL-2r promoter (in particular, that of the IL-2rα chain), or under the control of the HIV-1 LTR promoter. It is envisioned that the expression of genes under the control of promoters such as that of the IL-2rβ chain or HIV type 2 LTR or the LTR of similar retroviruses, can also be regulated by the rpt-1 proteins of the invention.

5.6. Anti-Rpt-1 Antibody Production

Antibodies can be produced which recognize the rpt-1 protein. Such antibodies can be polyclonal or monoclonal.

Various procedures known in the art may be used for the production of polyclonal antibodies to rpt-1. In a particular embodiment, rabbit polyclonal antibodies to an epitope of the rpt-1 molecule depicted in FIG. 2 can be obtained as described in Section 6.1.6, infra. For the production of antibody, various host animals can be immunized by injection with the native rpt-1 protein, or a synthetic version, or fragment thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

A monoclonal antibody to rpt-1 can be prepared by using any technique which provides for the production of antibody molecules by continuous cell lines in culture. These include but are not limited to the hybridoma technique originally described by Kohler and Milstein (1975, Nature 256:495–497), and the more recent human B-cell hybridoma technique (Kozbor et al., 1983, Immunology Today 4:72) and EBV-transformation technique (Cole et al., 1985, Monoclonal Antibodies and Cancer Therapy, Alan R. Liss, Inc., pp. 77–96).

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the 2 Fab or Fab fragments which can be generated by treating the antibody molecule with papain and a reducing agent.

5.7. Rpt-1-Related Derivatives, Analogues, and Peptides

The production and use of derivatives, analogues, and peptides related to rpt-1 are also envisioned, and within the scope of the present invention. Such derivatives, analogues, or peptides which have the desired immunogenicity or antigenicity can be used, for example, in immunoassays, for immunization, therapeutically, etc. Such molecules which retain, or alternatively inhibit, a desired rpt-1 property, e.g., down-regulation of IL-2r or HIV promoter-directed gene expression, can be used as inducers, or inhibitors, respectively, of such property. Derivatives, analogues, or peptides related to rpt-1 can be tested for the desired activity by procedures known in the art, including but not limited to the assays described in Sections 5.5 and 6.1.8.

The rpt-1-related derivatives, analogues, and peptides of the invention can be produced by various methods known in the art. The manipulations which result in their production can occur at the gene or protein level. For example, the cloned Rpt-1 gene can be modified by any of numerous strategies known in the art (Maniatis, T., 1982, Molecular Cloning, A Laboratory Manual, Cold Spring Harbor Laboratory, Cold Spring Harbor, N.Y.). The Rpt-1 sequence can be cleaved at appropriate sites with restriction endonuclease(s), followed by further enzymatic modification if desired, isolated, and ligated in vitro. In the production of the gene encoding a derivative, analogue, or peptide related to rpt-1, care should be taken to ensure that the modified gene remains within the same translational reading frame as rpt-1, uninterrupted by translational stop signals, in the gene region where the desired rpt-1-specific activity is encoded.

Additionally, the Rpt-1 gene can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551), use of TAB® linkers (Pharmacia), etc.

Manipulations of the rpt-1 sequence may also be made at the protein level. Any of numerous chemical modifications may be carried out by known techniques, including but not limited to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

In addition, analogues and peptides related to rpt-1 can be chemically synthesized. For example, a peptide corresponding to a portion of rpt-1 which mediates the desired regulation of gene expression can be synthesized by use of a DNA synthesizer (e.g., Applied Biosystems Model 380A).

5.8. Uses of Rpt-1

5.8.1. Diagnosis rpt-1 proteins, analogues, derivatives, and subsequences thereof, and anti-rpt-1 antibodies, have uses in diagnostics. The molecules of the invention can be used in assays, such as immunoassays, to detect, prognose, diagnose, or monitor various conditions, diseases, and disorders affecting T lymphocyte activation. For example, the amount of rpt-1 expressed in T cells appears to be inversely proportional to the amount of IL-2r present on the cell-surface (see Section 6.2 infra, FIG. 6A), which is a measure of T cell activation. Thus, in a specific embodiment, antibody to rpt-1 can be used to assay in a patient tissue or serum sample for the presence of rpt-1, where a decreased level of rpt-1 is an indicator of increased IL-2r cell-surface expression and T cell (immune) activation. In another embodiment, the detection of increased expression of rpt-1 can be viewed as a signal of decreased IL-2r cell-surface expression, which may be indicative of poor T cell responses and relative T cell resistance to activation. It is envisioned that various immune abnormalities such as congenital and acquired immune deficiencies, autoimmune disorders (e.g., systemic lupus erythematosus, rheumatoid arthritis, and diabetes type I), and various cancers may be susceptible to classification according to the levels found in patient samples of various immune function mediators, including rpt-1. Such classifications can be of great value in the prognosis or diagnosis of immune abnormalities.

The immunoassays which can be used include but are not limited to competitive and non-competitive assay systems using techniques such as radioimmunoassays, ELISA (enzyme linked immunosorbent assay), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays, and immunoelectrophoresis assays, to name but a few.

Rpt-1 genes and related nucleic acid sequences and subsequences, including complementary sequences, can also be used in hybridization assays. The Rpt-1 nucleic acid sequences, or subsequences thereof comprising about at least 15 nucleotides, can be used as hybridization probes. Hybridization assays can be used to detect, prognose, diagnose, or monitor conditions, disorders, or disease states associated with changes in rpt-1 expression as described supra. For example, total RNA in peripheral blood lymphocytes from a patient can be assayed for the presence of Rpt-1 mRNA, where the presence or amount of Rpt-1 mRNA is indicative of a state of T cell activation associated with an immune abnormality.

5.8.2. Therapy

The rpt-1 proteins, analogues, derivatives, and subsequences thereof, anti-rpt-1 antibodies, and Rpt-1 nucleic acids and subsequences thereof of the invention can be used for therapy of diseases or disorders associated with expression of products encoded by sequences whose transcription is controlled by an IL-2r promoter or a promoter of an LTR of a human lymphotropic retrovirus. For example, an Rpt-1 coding sequence can be incorporated into an hematopoietic stem cell for use in gene therapy of AIDS patients, where it will be expressed, causing decreased expression of HIV-1-LTR-directed genes. In another embodiment, rpt-1 may be used to regulate gene expression of HTLV-I or HTLV-II in leukemic patients. The rpt-1 protein itself can be conjugated with an anti-nuclear protein antibody or anti-DNA antibody in order to effect proper targeting of the rpt-1 molecule.

Various delivery systems are known and can be used for therapeutic delivery of rpt-1 and related molecules, e.g., encapsulation in liposomes, expression by bacteria, etc. Other methods of introduction include but are not limited to intradermal, intramuscular, intraperitoneal, intravenous, subcutaneous, and intranasal routes.

In another embodiment of the invention, rpt-1, a related molecule, or antibody to rpt-1, which is shown to inhibit rpt-1 function, can be used in an attempt to increase T cell activation, e.g., of a patient who is immunosuppressed due to chemotherapy or radiation exposure.

6. CLONING AND CHARACTERIZATION OF THE RPT-1 GENE AND ITS ENCODED PROTEIN

In the examples section herein, we describe a regulatory protein T-lymphocyte-1 (Rpt-1) gene, selectively expressed by resting relative to activated CD4+ helper-/inducer T cells, which encodes a novel intracellular protein (41,000 molecular weight) that down-regulates gene expression directed by the promoter region of the interleukin-2 receptor alpha chain (IL-2rα) gene and by the promoter region of the long terminal repeat of the human immunodeficiency virus type 1 (HIV-1). Our data suggest that rpt-1 levels may be inversely correlated with activation of CD4+T cells and HIV-1 replication leading to clinical symptoms of the acquired immune deficiency syndrome (AIDS).

In additional experiments, we have demonstrated specific regulation by rpt-1 of gene expression controlled by a promoter of HTLV-II or HTLV-I, but not by a promoter of herpes simplex virus thymidine kinase or SV40.

6 1 Materials and Methods

6.1.1. Cells

The derivation and maintenance of T cell clones used herein have been described previously (Clayberger, C., et al., 1983, J. Exp. Med. 157:1906–1917; Clayberger, C., et al., 1984, J. Exp. Med. 158:1881–1894). Briefly, Cl.Ly1-T1 and Cl.Ly1-N5 are inducer T cell clones (id.). C1.NK-11 is a natural killer cell clone (Nabel, G., et al., 1981, Proc. Natl. Acad. Sci. U.S.A. 78:1157–1161) and Cl.Ly23.4 is a suppressor T cell clone (Fresno, M., et al., 1981, J. Exp. Med. 153:1260–1274). Ar-5 is an arsonate-reactive inducer T cell clone (Rao, A., et al., 1983, J. Exp. Med. 159:1243–1258). Ar-5v is a variant of Ar-5 that constitutively expresses high levels of IL-2rα (as measured by immunofluorescence using a monoclonal antibody, AMT-13, to the IL-2rα chain, supplied by Boehringer Mannheim). Ar-5v, but not Ar-5, is activated by recombinant IL-2 (Genzyme) in the absence of antigen; activation is completely blocked by AMT-13. Ar-5v does not produce detectable levels of IL-2 unless activated by IL-2 or antigen and IA$^d$ macrophages. Jurkat (Nabel, G. and Baltimore, D., 1987, Nature 326:711–713) and EL-4 are human and murine T cell lines, respectively, and COS7m6 is an SV40-transformed monkey kidney epithelial cell line (Okayama, H., and Berg, P., 1983, Mol. Cell. Biol. 3:280–289).

6.1.2. Activation of T Cells

Resting T cell clones were activated by antigen (Clayberger, C., et al., 1983, J. Exp. Med. 157:1906–1917; Clayberger, C., et al., 1984, J. Exp. Med. 158:1881–1894; Nabel, G., et al., 1981, Proc. Natl. Acad. Sci. U.S.A. 78:1157–1161; Fresno, M., et al., 1981, J. Exp. Med. 153:1260–1274) or by addition of 5 ug/ml of concanavalin A (ConA) and 10 ng/ml of 12-0-tetradecanoylphorbol 13-acetate (TPA). Jurkat cells were activated by the addition of TPA (40 ng/ml) and phytohemagglutinin (PHA) (10 ug/ml). EL-4 cells were activated by the same amounts of TPA and PHA in addition to calcium ionophore A23187 (5 ug/ml).

6.1.3. Production of a T Cell Probe

Poly(A)+ RNA from L cells (a fibroblast tumor) and from 2PK3 (a B cell lymphoma) was prepared and hybridized to $^{32}$P-labelled cDNA obtained from Cl.Ly1-TI cells (22 hours after activation) as described previously (Chirgwin, J., et al., 1979, Biochemistry 18:5294–5299; Freeman, G. J., et al., 1983, Proc. Natl. Acad. Sci. U.S.A. 80:4094–4098). The remaining single-stranded cDNA purified by hydroxyapatite chromatography was hybridized with poly(A)+ RNA from MOPC 315 (a B cell myeloma) and the single-stranded fraction was again isolated by hydroxyapatite chromatography.

6.1.4. Construction of a T Cell cDNA Library

Poly(A)+ RNA from Cl.Ly1-T1 (22 hours after activation) was used to prepare a cDNA library of $3.8 \times 10^5$ independent clones in the pcD vector (Okayama, H. and Berg, P., 1982, Mol. Cell. Biol. 2:161–170; Okayama, H. and Berg, P., 1983, Mol. Cell. Biol. 3:280–289). 11,300 colonies, from a 0.5 to 20 kb cDNA insert size-selected sublibrary were sparsely plated on nitrocellulose and then probed (Maniatis, T., et al., 1982, Molecular Cloning, A Laboratory Manual, Cold Spring Harbor Laboratory, Cold Spring Harbor, N.Y.) with the T cell specific probe described above. Positively hybridizing colonies were picked for further analysis.

6 1.5. Nucleic Acid Blotting and Hybridization

RNA slot and Northern blots were performed as described (Chirgwin, J., et al., 1979, Biochemistry 18:5294–5299). The same amount of total RNA was used for every sample of a given experiment. Southern blots were carried out as described by Gatt et al. (1984, Biotechniques 2:148–155).

6.1.6. Western Blot Analysis

Mouse spleen cells ($10^7$–$10^8$) were washed twice with PBS and resuspended in 1 ml of lysis buffer (1% NP-40, 0.02% NaN$_3$ in PBS), 10 ul of phenylmethylsulfonyl fluoride (PMSF) (34.8 mg in 1 ml methanol) and 20 ul iodoacetamide (36.2 mg in 0.5 ml distilled H$_2$O). The mixture was incubated on ice for 30 minutes and loaded onto a polyacrylamide gel. After transfer of proteins from the polyacrylamide gels to nitrocellulose sheets (Towbin, H., et al., 1979, Proc. Natl. Acad. Sci. U.S.A. 76:4350–4354), the filters were incubated for one hour with pro-binding protein (5% milk protein, 1% fetal calf serum in Tris saline azide (TSA)) and rabbit IgG (1:200 serum dilution) obtained after immunization with keyhole limpet hemocyanin (KLH) conjugated to a synthetic peptide corresponding to the most hydrophilic portion of the rpt-1 protein (KKEKKE) (FIG. 3), followed by a 30 minute incubation with an $^{125}$I-labelled goat anti-rabbit antibody. Filters were washed with TSA and exposed for autoradiography.

6.1.7. Plasmids 230 of 11,300 colonies from the size selected cDNA library (Shen, F.-W., et al., 1985, Proc. Natl. Acad. Sci. U.S.A. 82:7360–7363) described supra hybridized with the T cell cDNA probe described above. Plasmid pcD-rpt-1 was obtained from a hybridizing colony. pcD-rpt-1 DNA hybridized to a 3.7 kb RNA expressed in T cells (see Section 6.2). pcD-rpt1fs is a frame-shift mutant of pcD-rpt1 obtained by digesting pcD-rpt1 with the enzyme BstEII, blunt-ending with T4 polynucleotide kinase, and religating. The mutation was confirmed by DNA sequencing. pSV2CAT contains the SV40 enhancer-promoter region upstream of the bacterial chloramphenicol acetyl transferase (CAT) gene (Gorman, C. M., et al., 1982, Mol. Cell. Biol. 2:1044–1051). The plasmid IL2rpCAT contains the human IL-2rα promoter region upstream of CAT (Leonard, W. J., et al., 1985, Science 230:633–639). The plasmid pLTR-1CAT contains the U3 and R regions of the HIV-1 long terminal repeat (LTR) (nucleotides −463 to +80) (Tong-Starksen, S. E., et al., 1987, Proc. Natl. Acad. Sci. U.S.A. 84:6845; Sanchez-Pescador, R., et al., 1985, Science 227:484–492). pSV7fdtat is an expression vector for the tat protein of HIV-1 (id.).

6.1.8. Transfection of Cell Lines and Chloramphenicol Acetyl Transferase Assays The DEAE-dextran technique (Queen, C. and Baltimore, D., 1983, Cell 33:741–748) was used to transfect adherent cells ($10^6$ cells/transfection) and cells grown in suspension ($10^7$ cells/transfection). 48 hours after transfection, CAT lysates were prepared by freeze-thawing (Gorman, C. M., et al., 1982, Mol. Cell. Biol. 2:1044–1051). Assays were done with equivalent amounts of protein from each lysate (approximately 200–300 ug protein per assay) as described (id.), except that the final acetyl coenzyme A concentration in the reaction mix was 3 mM. Reaction mixes were evaluated for percent conversion of chloramphenicol to acetylated forms, at different time points, by thin layer chromatography. Experiments were done in the linear range of the assay, and were repeated three to five times with different batches of purified DNA. Extracts from cells that had not been transfected with CAT plasmids showed no CAT activity. Expression of the Rpt-1 cDNA insert was confirmed at both the protein level (by FACS) and the RNA level (by slot blots using the SV40 polyadenylation signal region from the pcD vector as hybridization probe, to avoid hybridization with endogenous rpt-1 in T cells). COS and Jurkat cells transfected with pcD-rpt1 expressed the recombinant protein while those transfected with pcD-rpt1fs did not. Activation of Jurkat cells did not significantly change the levels of the recombinant protein according to FACS analysis. Southern blot analysis revealed that equivalent amounts of plasmid were transfected in every case.

6.1.9. Immunofluorescence rpt-1: Cells were placed on coverslips, incubated with 0.5% glutaraldehyde for 30 seconds, washed, and incubated with the IgG fraction of a rabbit anti-KKEKKE antiserum at 1:200 final concentration, at 4° C. for 40 minutes. The cells were then washed twice with 1 X PBS before addition of rhodamine-conjugated goat anti-rabbit IgG (1:100 dilution) (Cooper Biomedical, Glendale, Calif.).

Cell surface antigens: Thy1+ and Ig+ spleen cells (Fresno, M., et al., 1982, Cell 30:707–713; Clayberger, C., et al., 1984, J. Exp. Med. 158:1881–1894; Fresno, M., et al., 1981, J. Exp. Med. 153:1260–1274) were incubated with either AMT-13, L3T4, or Ly2 monoclonal antibodies (Becton-Dickinson, Mountainview, Calif.), washed thrice and incubated with fluorescein isothiocyanate (FITC)-goat anti-rat IgG (1:200 dilution) (Cappel, Westchester, Pa.). The intensity of fluorescence of each cell population analyzed by FACS is presented on a $\log_{10}$ scale (FIGS. 4, 6). Where indicated, cells were visualized using a fluorescent photomicroscope (Olympus IMT2) with barrier filters of 420 to 490 nm for fluorescein, and 500 to 590 nm for rhodamine.

6.2. Results

After activation by antigen or by the T cell mitogen concanavalin A, the T cell clone Cl.Ly1-T1 undergoes one or two rounds of division and secretes inducer-specific proteins (Nabel, G., et al., 1981, Cell 23:19–28; Clayberger, C., et al., 1984, J. Exp. Med. 158:1881–1894). 230 of the 11,300 colonies from a size-selected Cl.Ly1-T1 pcD cDNA library hybridized to a cDNA probe enriched for genes expressed in T cells. One of these inserts, termed Rpt-1 (regulatory protein T cell), hybridized to a 3.7 kb mRNA present in inducer T cell clones (FIG. 1A, lanes e–h), but not in a suppressor T cell clone (FIG. 1A, lanes c,d), a natural killer cell clone (FIG. 1A, lane b), or a cytolytic T cell clone (FIG. 1A, lane a). Expression was not dependent on long-term growth of T cell clones since the Rpt-1 probe hybridized to a 3.7 kb RNA from freshly explanted lymphoid cells of the spleen and thymus (FIG. 1B).

Resting inducer T cells (FIG. 1A, lanes e,g) showed higher levels of Rpt-1 RNA than activated inducer T cells (FIG. 1A, lanes f,h). Analysis of the time course of Rpt-1 expression during activation of Cl.Ly1-T1 with antigen and splenic adherent cells showed that Rpt-1 transcription was not detectable four to eight hours after activation (upper panel, FIG. 1C). Expression of other genes we have studied, including T cell-specific genes, is either unchanged or, more commonly, increased after activation, as illustrated by Northern blot analysis of gamma-interferon RNA (lower panel, FIG. 1C).

The complete nucleotide sequence of the full length Rpt-1 clone cDNA insert was determined using the Maxam and Gilbert method (Maxam, A. M., and Gilbert, W., 1977, Proc. Natl. Acad. Sci. U.S.A. 74:560–564). The total sequence of 3700 bp contains an open reading frame 353 amino acids long (positions 165 to 1226) (FIG. 2), followed by a very long 3′-untranslated region of 2466 bp with several potential polyadenylation signals. The first methionine in this open reading frame is encoded by a subsequence that fits the consensus for eukaryotic translation initiation signals (Kozak, M., 1984, Nucl. Acids Res. 12:857–872). The predicted protein has a molecular weight of 41,330 daltons, is relatively neutral in charge (pI of 6.29), and includes a potential N-linked glycosylation site (amino acid residue numbers 30 to 32). However, the lack of an obvious signal sequence or membrane spanning region (Sabatini, D. D., et al., 1982, J. Cell. Biol. 92:1–19) makes it unlikely to be a membrane-bound protein.

Additional experiments have indicated the existence of a "silencer" sequence in the 3′ untranslated region of the Rpt-1 gene, to which a T cell-specific protein binds, thereby decreasing transcription levels of Rpt-1 mRNA. The strain-specific polymorphism associated with different levels of Rpt-1 expression (FIG. 5) resides within the silencer region, as judged by Southern blot hybridization using a cDNA probe corresponding to a portion of the 3' untranslated region of the Rpt-1 gene.

Western blot analysis (as described in Section 6.1.6) of mouse spleen cell extracts using radiolabeled antibodies raised to a synthetic peptide (KKEKKE) that corresponds to the predicted most hydrophilic region of the rpt-1 protein (Hopp, T., and Woods, K., 1981, Proc. Natl. Acad. Sci. U.S.A. 78:3824-3828) (FIGS. 2,3), revealed a protein of the expected molecular weight (FIG. 4A). Immunofluorescent analysis with fluorescein-conjugated anti-KKEKKE antibody was used to determine the expression of rpt-1 in different lymphoid lineages (see Section 6.1.9). Less than 0.3% of splenic Ig+ cells (B cells), less than 2% of Ly2+ T cells, and 78–91% of L3T4+ cells were positive for rpt-1.

The carboxyl-terminal half of rpt-1 has a subsequence (TVPQKRKRT; amino acid residue numbers 268 to 276, FIG. 2) similar to the nuclear localization signal of the simian virus 40 (SV40) large T antigen (FIG. 3) (Kalderon, D., et al., 1984, Cell 39:499–509), which may interact with a receptor in the nuclear envelope (Goldfarb, D. S., et al., 1986, Nature 322:641–644). COS7m6 cells transfected with the expression vector pcD-rpt1, but not with pcD-rpt1fs (a frame shift mutant of rpt-1, see Section 6.1.7), were positive for rpt-1 expression, as measured by immunofluorescence using anti-KKEKKE antibody and detected by FACS analysis (FIG. 4B); microscopic observation showed predominantly nuclear staining (FIG. 4C).

The amino-terminal half of the rpt-1 protein contains pairs of cysteine residues (FIGS. 2 and 3) in the following pattern: $Cys-X_2-Cys-X_{16}-Cys-X_2-Cys-X_{16}-Cys-X_2Cys$. These cysteine residues are unlikely to be involved in disulfide bridge formation in view of conditions in the intracellular environment. This organization of cysteine residues is a prominent feature of proteins involved in metal binding and regulation of gene expression (reviewed in Berg, J., 1986, Science 232:485–487). The cysteine residues are believed to bind metals such as zinc while the intervening amino acids protrude in a finger-like projection. The rpt-1 protein has the potential to form two alternative fingers (FIG. 3). Secondary structure algorithms (Hopp, T. and Woods, K., 1981, Proc. Natl. Acad. Sci. U.S.A. 78:3824–3828; Chou, P. Y. and Fasman, G. D., 1978, Ann. Rev. Biochem. 47:251–276) predict that the regions containing the cysteine pairs are hydrophobic and in a beta sheet configuration, while the intervening segments representing finger-like projections are hydrophilic and include a beta-turn (FIG. 3). There is an additional pair of cysteine residues in the rpt-1 protein followed by a pair of histidines with the potential to form a metal finger (FIG. 3).

To determine whether the Rpt-1 gene maps to any of the loci that are thought to affect T cell function, we located the genetic linkage of Rpt-1 using restriction fragment length polymorphisms (RFLP) present in recombinant inbred strains derived from C57Bl/6 (B) and DBA (D) strains. Genomic DNA was digested with HindIII, and the 5' 1.3 kb Rpt-1 coding region insert (RsaI-XbaI fragment) was used as a hybridization probe. Since the B strain DNA digest shows a major band of 10 kb and minor bands of 9.5, 4, 2, 1, and 0.8 kb, whereas the D strain DNA shows a major band of 9 kb and minor bands of 12, 10, and 1 kb, each BXD strain could be unambiguously assigned a parental origin and correlated with the genetic maps of the 26 BXD strains. This analysis indicated linkage to HBB, the hemoglobin b chain locus on chromosome 7 (FIG. 5).

A polymorphism that affects expression of IL-2rα on L3T4+ inducer T cells (but not Ly2+ T cells) also maps to the HBB locus using BXD lines (Kawamura, H., et al., 1986, J. Exp. Med. 163:1376–1390). Analysis of the relationship between expression of rpt-1 and IL-2rα on different T cell clones showed an inverse correlation (FIG. 6A). Moreover, T cells transfected with pcD-rpt1, but not pcD-rpt1fs cDNA, pcD, or pcD-betagalactosidase, showed reduced levels of IL-2rα (assessed by FACS analysis, FIG. 6A); slot blot analysis of these transfectants confirmed a decrease in IL-2r mRNA while levels of IL-3 mRNA were unchanged. The experiments described infra were performed to determine whether inhibition of IL-2rα expression after Rpt-1 transfection reflected a direct effect of rpt-1 on IL-2rα gene expression.

Co-transfection of pcD-rpt1, compared with pcD-rpt1fs (FIG. 6B, lanes 1,2; see Section 6.1.8), pcD, or pcD-betagalactosidase, resulted in a 3–5 fold down-regulation of gene expression directed by the human IL-2rα promoter in COS7m6 cells (FIG. 6B, lanes 1,2). In contrast, pcD-rpt1 transfection had no effect on gene expression directed by the SV40 enhancer-promoter (plasmid pSV$_2$CAT) (FIG. 6B, lanes 5,6) and the adenoviral thymidine kinase promoter.

We investigated the effects of rpt-1 on other inducer-specific cellular and retroviral genes. Co-transfection of pcD-rpt1, but not pcD-rpt1fs, resulted in a three-fold inhibition of HIV-1 LTR-directed gene expression in COS7m6 cells (FIG. 6B, lanes 3,4). We also performed these cotransfection assays with T lymphocytes. Resting T cells contain endogenous rpt-1, and the HIV-1 LTR is expressed at near background levels in these cells (Nabel, G. and Baltimore, D., 1987, Nature 326:711–713; Tong-Starksen, S. E., et al., 1987, Proc. Natl. Acad. Sci. U.S.A. 84:6845); the low baseline level of HIV-1 LTR expression makes it difficult to detect inhibition of expression after transfection of exogenous cDNA. Therefore, we tested the effect of rpt-1 on HIV-1 LTR-directed gene expression in the presence of the HIV-1 trans-activator protein, tat. A three-fold inhibition was observed in resting Jurkat and EL-4 cell lines in the presence of HIV-1 tat (FIG. 6B). However, no inhibition of HIV-1 LTR-directed gene expression, in the presence or absence of HIV-1 tat, was seen after activation of these T cell lines (FIG. 6B).

In cotransfection experiments similar to those described supra, we have demonstrated specific regulation by rpt-1 of gene expression controlled by the promoters of the human retroviruses HTLV-I and HTLV-II, but not by the promoters of herpes simplex virus thymidine kinase or of SV40.

6.3. Discussion

Potential metal-binding fingers in the amino-terminal half (reviewed in Berg, J., 1986, Science 232:485–487) and a stretch of predominantly charged amino acids in the carboxy-terminal portion (Legrain, M., et al., 1986, Nucl. Acids Res. 14:3059–3073; Keegan, L., et al., 1986, Science 231:699–704; Hope, J. and Struhl, K., 1986, Cell 46:885–894) are features of several proteins that regulate gene expression. The marked difference of character between the amino- and carboxy-terminal halves of the rpt-1 protein may denote at least two functional domains, as in the case of Xenopus transcription factor IIIA (Miller, J., et al., 1985, EMBO J. 4:1609–1614): an amino-terminal domain that targets the protein to a particular set of nucleic acids and a carboxy-terminal domain that exerts regulatory activity. Rpt-1 may affect IL-2rα and HIV-1 expression through cis-acting negative regulatory elements or through competition with proteins that bind to enhancer or activator sequences. rpt-1 may directly bind to regions of the IL2rα and HIV-1 promoter, such as those sequences that are reported to be similar (Fugita, T., et al., 1986, Cell 46:401–407).

We have determined, by S1 mapping analysis, that decreased levels of gene expression directed by the human IL-2rα promoter can be ascribed to a decrease in full-length RNA levels (rather than a shift in the transcriptional start site). Although decreased gene expression was only three to five fold as assessed by CAT assays, this inhibition was physiologically significant since a substantial fraction (approximately ½) of cells transfected with rpt-1 no longer displayed surface levels of IL-2rα required for activation by IL-2 (FIG. 6A; Lethe Bich-Thuy, et al., 1987, J. Immunol. 139:1550–1556). The regulation of human IL2-rα- and HIV-1, HTLV-I, and HTLV-II LTR-directed gene expression by rpt-1 indicates that this recombinant product is biologically active across species. By FACS analysis of Jurkat cells (a human T cell line) with the anti-KKEKKE antibody, we have detected a related protein whose levels are undetectable 16 hours after activation.

The hallmark of HIV-1 associated diseases is a relatively long asymptomatic period concurrent with evidence for low level persistent infection (Klatzmann, D. and Gluckman, J. C., 1986, Immunol. Today 7:291–296). One explanation of HIV-1 latency comes from low levels of NF-Kappa B (Nuclear Factor Kappa B; Nabel, G. and Baltimore, D., 1987, Nature 326:711–713; Tong-Starksen, S. E., et al., 1987, Proc. Natl. Acad. Sci. U.S.A. 84:6845) in resting T cells. Activated T cells contain increased levels of the NF-Kappa B factor or its functional equivalent, which interacts with the HIV-1 enhancer sequence to induce elevated levels of HIV-1 LTR-directed gene expression (id.). The observed failure of rpt-1 to down-regulate HIV-1 LTR-directed gene expression in stimulated T cells suggests that NF-Kappa B is dominant in the activated state.

The expression of the Rpt-1 gene in resting CD4+ T cells provides an additional basis for the latent state of HIV-1. rpt-1 directly inhibits HIV-1 gene expression even in the presence of significant amounts of tat protein (FIG. 6B), and prevents expression of surface levels of IL-2rα required for efficient IL-2 mediated activation (Lethe Bich-Thuy, et al., 1987, J. Immunol. 139:1550–1556) (FIG. 6, A and B). A consequence of these activities should be limitation of HIV-1 mediated destruction to clones of CD4+ cells that are specifically activated by antigenic determinants, after exposure of the immune system to bacteria and viruses. Expression of Rpt-1 in the remaining CD4+ clones may preempt secondary activation by IL-2 and efficient expression of HIV-1, which may account for the slow decay of CD4+ T cells despite chronic HIV-1 infection. It is possible that rpt-1 levels in inducer T cells may be inversely correlated with increased HIV-1 replication responsible for the clinical symptoms of AIDS.

7. DEPOSIT OF MICROORGANISMS

*E. coli* strain MC1061 carrying plasmid pcD-rpt-1 has been deposited with the Agricultural Research Culture Collection (NRRL), Peoria, Ill., and has been assigned accession number B-18297.

The present invention is not to be limited in scope by the microorganisms deposited since the deposited embodiment is intended as a single illustration of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for the purpose of description.

What is claimed is:

1. An isolated and purified DNA sequence as shown in FIG. 2.
2. The sequence of claim 1 which comprises a cDNA sequence.
3. The sequence of claim 1 which comprises a genomic DNA sequence.
4. An RNA sequence complementary to the DNA sequence of FIG. 2.
5. An isolated and purified DNA sequence comprising a sequence substantially homologous to the nucleotide sequence shown in FIG. 2 or a portion thereof which encodes a protein or polypeptide which is capable of decreasing the expression of genes under the control of the interleukin 2 receptor alpha chain promoter or the long terminal repeat of the human immunodeficiency virus type 1.
6. A recombinant vector containing the DNA sequence of claim 1.
7. A recombinant vector containing the DNA sequence of claim 5.
8. The recombinant DNA vector comprising pcD-rpt-1.
9. An isolated cell containing the vector of claim 6 or 7.
10. An isolated cell containing the vector of claim 8.
11. The isolated cell of claim 9 which is mammalian.
12. The isolated cell of claim 10 which is mammalian.
13. The isolated cell of claim 9 which comprises a bacterium.
14. The isolated cell of claim 10 which comprises a bacterium.
15. The bacterium of claim 14 comprising an *Escherichia coli* as deposited with the NRRL and assigned accession number B-18297, or a mutant, or genetically engineered derivative thereof which encodes a protein or polypeptide which is capable of decreasing the expression of genes under the control of the interleukin 2 receptor alpha chain promoter or the long terminal repeat of the human immunodeficiency virus type 1.
16. A method for regulating gene expression controlled by a promoter of the interleukin-2 receptor alpha chain gene comprising (1) introducing a nucleic acid sequence encoding the rpt-1 protein as shown in FIG. 2 or biologically active fragment thereof into a host cell, and (2) subjecting said host cell to conditions such that the rpt-1 protein is expressed in amounts sufficient to regulate said gene expression within said host cell.

17. A method for regulating gene expression controlled by a promoter of a long terminal repeat of a human lymphotropic retrovirus comprising (1) introducing a nucleic acid sequence encoding the rpt-1 protein as shown in FIG. 2 or a biologically active fragment thereof into a cell infected by a human lymphotropic retrovirus, and (2) subjecting said host cell to conditions such that the rpt-1 protein is expressed in amounts sufficient to regulate said gene expression within said host cell.

18. The method according to claim 17 in which the retrovirus comprises human immunodeficiency virus type I.

19. The method according to claim 17 in which the retrovirus comprises human T cell leukemia virus type I.

20. The method according to claim 17 in which the retrovirus comprises human T cell leukemia virus type II.

21. The method according to claim 16 in which the regulation results in a decrease in the level of gene expression.

22. The method according to claim 17 in which the regulation results in a decrease in the level of gene expression.

23. The method according to claim 18 in which the regulation results in a decrease in the level of gene expression.

* * * * *

UNITED STATES PATENT AND TRADEMARK OFFICE
CERTIFICATE OF CORRECTION

PATENT NO. : 4,952,499

DATED : August 28, 1990

INVENTOR(S) : Cantor et al.

It is certified that error appears in the above-identified patent and that said Letters Patent is hereby corrected as shown below:

On the Title page; item [75],
Inventors should read: Harvey I. Cantor, Wellesley; Roberto Patarca, Brookline; Gordon J. Freeman, Brookline, all of Mass.

Signed and Sealed this

Twenty-seventh Day of April, 1993

Attest:

MICHAEL K. KIRK

Attesting Officer    Acting Commissioner of Patents and Trademarks